(12) United States Patent
Miyahara et al.

(10) Patent No.: US 11,033,479 B2
(45) Date of Patent: *Jun. 15, 2021

(54) ALPHA-GEL FORMING COMPOSITION AND ALPHA-GEL COMPOSITION

(71) Applicant: SHISEIDO COMPANY, LTD., Tokyo (JP)

(72) Inventors: Reiji Miyahara, Yokohama (JP); Tetsuro Yonezawa, Yokohama (JP); Takashi Oka, Yokohama (JP); Makoto Uyama, Yokohama (JP); Saori Tanabe, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 498 days.

This patent is subject to a terminal disclaimer.

(21) Appl. No.: 16/073,201

(22) PCT Filed: Jan. 6, 2017

(86) PCT No.: PCT/JP2017/000243
§ 371 (c)(1),
(2) Date: Jul. 26, 2018

(87) PCT Pub. No.: WO2017/130655
PCT Pub. Date: Aug. 3, 2017

(65) Prior Publication Data
US 2021/0100732 A1    Apr. 8, 2021

(30) Foreign Application Priority Data

Jan. 27, 2016 (JP) .............................. JP2016-013181

(51) Int. Cl.
| | |
|---|---|
| *A61K 8/86* | (2006.01) |
| *A61K 8/34* | (2006.01) |
| *A61Q 19/00* | (2006.01) |
| *C08L 71/02* | (2006.01) |
| *A61K 8/39* | (2006.01) |
| *A61K 8/04* | (2006.01) |
| *A61K 8/36* | (2006.01) |
| *A61Q 17/04* | (2006.01) |
| *A61K 8/06* | (2006.01) |

(52) U.S. Cl.
CPC .............. *A61K 8/86* (2013.01); *A61K 8/042* (2013.01); *A61K 8/06* (2013.01); *A61K 8/342* (2013.01); *A61K 8/361* (2013.01); *A61K 8/39* (2013.01); *A61Q 17/04* (2013.01); *A61Q 19/00* (2013.01); *C08L 71/02* (2013.01); *A61K 2800/52* (2013.01); *A61K 2800/594* (2013.01); *C08L 2201/08* (2013.01); *C08L 2201/54* (2013.01); *C08L 2205/025* (2013.01)

(58) Field of Classification Search
CPC . A61K 8/345; A61K 8/37; A61K 8/86; A61K 8/92; A61K 8/042; A61K 8/342; A61K 8/39; A61K 8/922; A61K 2800/52; A61K 8/02; A61K 8/63; A61Q 19/00; A61Q 19/10; A61Q 5/02; C08K 5/04; C08L 71/02

See application file for complete search history.

(56) References Cited

U.S. PATENT DOCUMENTS 10,898,426 B2 * 1/2021 Miyahara ............... A61K 8/064
2007/0166270 A1   7/2007 Neuss

FOREIGN PATENT DOCUMENTS

| FR | 2539324 | * 1/1994 | ............. B01F 17/00 |
| WO | WO 2010/090219 | 8/2010 | |
| WO | WO 2015/021382 | * 2/2015 | ............. A61K 33/00 |
| WO | WO 2015 190306 | 12/2015 | |

OTHER PUBLICATIONS

Lomdardo (Advances in Condensed Matter Physics, vol. 2015, 1-22; 2015) (Year: 2015).*
Serial No. TW 10921126960, Taiwan Notification Letter of Examination Opinion from Intellectual Property Bureau of Ministry of Economic Affairs, dated Nov. 20, 2020, 2 pages—English, 3 pages—Chinese.
PCT/JP2017/000243 Written Opinion and International Search Report, dated Apr. 4, 2017, 8 pages—English, 7 pages—Japanese.
"The viscosity stability of O/W emulsion containing α-gel through an ionic-complex system", by Uyama, Ikula, Teshigawara, Watanabe and Miyahara, Journal of Oleo Science (SSN-1345-8957), Copyright 2013 by Japan Oil Chemists Society, http://www.jstage.jst.go.jp/browse/jos/, dated Jul. 14, 2012, 8 pages (pp. 9-16).
"α-gel Prepared in Sodium Methyl Stearoyl Taurate/Behenyl Alcohol/Watere System—Characterization of Structural Changes with Water Concentration", by Watanabe, Inoue, Teshigawara and Kimura, Journal of Oleo Science, Copyright 2013 by Japan Oil Chemists Society, Accepted Aug. 24, 2011, http://www.jstage.jst.go.jp/browse/jos/, 6 pages (pp. 29-34).

(Continued)

*Primary Examiner* — Anna R Falkowitz
(74) *Attorney, Agent, or Firm* — Andrew F. Young, Esq.; Nolte Lackenbach Siegel

(57) ABSTRACT

The present invention provides an α-gel forming composition and an α-gel composition that uses an α-gel formation composition that is highly stable and that does not become colored or deposit crystals, etc. over time. An α-gel composition includes (A) 25-50 mass % of one or more higher aliphatic alcohol and/or higher fatty acid has 16 or more carbons, (B) 40-70 mass % of a specific polyoxyethylene sterol ether, and (C) 5-20 mass % of a specific polyoxyethylene dialkyl ester and/or ether. The α-gel composition is generated by adding water.

5 Claims, 3 Drawing Sheets

(56) References Cited

OTHER PUBLICATIONS

"Applications of Phospholipid to Cosmetics", by Konno, Skin-care Product Development Laboratories, Research Laboratories, KOSE Corporation, J. Soc. Cosmet. Chem. Jpn., vol. 45, No. 2, 2011, 1 page—English, 8 pages—Japanese (pp. 83-90).
PCT/JP2017/000243 filed Jan. 6, 2017.
JP 2016-013181 filed Jan. 27, 2016.
PCT/JP2017/003070, Written Opinion and International Search Report, dated Apr. 4, 2017, 4 pages—English, 7 pages—Japanese.
The viscosity stability of O/W emulsion containing α-gel through an ionic-compex system, by Uyama, Ikuta, Teshigawara, Watnabe, Miyahara, Journal of Oleo-Science, Copyright 2013 by Japan Oil Chemists' Society, J. Oleo Sci. 62 (1) Sep. 16, 2013, , http://www.jstage.jst.go.jp/browse/jos/, pp. 9-16.
α-Gel Prepared in Sodium Methyl Stearoyl Taurate/Behenyl Alcohol/Water system—Characterization of Structural Changes with Water Concentration, by Watanabe, Inoue, Teshigawara and Kimura, Jouranal of Oleo Science, Copyrigh 2012 by Japan Oil Chemists' Society, J. Oleo Sci. 61 (1) 29-334 (2012), http://www.jstage.jst.go.jp/browse/jos/, pp. 29-34.
A Study on skin hydration with cream, by Nishiyama, Komatsu, Tanaka, Shiseido Laboratories, J. Soc. Cosmet. Chem. Japan, vol. 16 No. 2 1983, pp. 136-143, English abstract and partial translation throughout.
Formation of Pseudo-Intercellular Lipids Membrance on the Skin Surface by the Alpha-Gel Holding a Large Amount o fWater, by Orita, Uchiyama, Hanamoto, Yamashita, Naitou, Takeuchi, Katayama, Tanabe, Fukuda, Okada, Journal of Japan Cosmetic Engineers, vol. 46, No. 1 2012, pp. 25-32, English abstract and partial translation throughout.
EP 17743889.2, Extended European Search Report, dated Jun. 3, 2019, 5 pages—English.
Database GNPD, Skin Reset Cream, Record ID: 3079393, Somme Institute, published Apr. 2015, http://www.gnpd.com, 5 pages—English.
U.S. Appl. No. 16/509,901, filed Jul. 12, 2019, Notice of Allowance dated Nov. 16, 2020, 7 pages.

* cited by examiner

ALPHA-GEL FORMING COMPOSITION AND ALPHA-GEL COMPOSITION

RELATED APPLICATIONS

This application claims the priority of as a § 371 national phase of Ser. No.: PCT/JP2017/000243 filed Jan. 6, 2017, the entire contents of which are incorporated herein by reference which in turn claims priority from Japanese Patent Application No. 2016-013181 filed on Jan. 27, 2016, which is incorporated herein by reference.

TECHNICAL FIELD

The present invention relates to a composition for forming α-gel (α-gel forming composition) and an α-gel composition, and particularly to improvement of α-gel forming substance.

BACKGROUND OF THE INVENTION

An α-Gel-containing external skin care preparations, which use α-gel formed by a higher aliphatic alcohol or a higher fatty acid and a hydrophilic surfactant, have been long used for the purpose of maintaining the emulsion stability of external skin care preparations such as cosmetics, quasi-drugs, and pharmaceutical products. Such α-gel has a high-viscosity and stabilizes an external skin care preparation but has problems of causing a slimy feel during application and easily depositing crystals of a higher alcohol or a higher fatty acid over time in terms of stability (e.g., see Non-Patent Literature 1).

Additionally, the increase in the viscosity over time commonly occurs and accordingly use of a double-chain cationic surfactant as a viscosity increase inhibitor has been investigated but sufficiently good stability has not yet been achieved (e.g., see Non-Patent Literature 2). Further, the effect on preventing water loss from the internal skin (occlusion) was not sufficient.

Further, for the purpose of preventing water loss from the internal skin, similar formulations containing a double-chain compound such as ceramide, a dialkyl quaternary ammonium salt, or phospholipid and sterol (e.g., Patent Literature 1), and formulations containing phospholipid, a polyoxyethylene sterol ether, higher alcohol (e.g., Patent Literature 2 and Non-Patent Literature 3) have been used, but phospholipids have the drawbacks of color development, a smell, and the like, and ceramide have the drawback of easily depositing crystals.

PRIOR ART DOCUMENTS

[Patent Literatures]
[Patent Literature 1] Japanese Patent No. 5609074
[Patent Literature 2] Japanese Patent No. 4495941
 [Non-Patent Literature]
[Non-Patent Literature 1] Kei Watanabe et al., J. Oleo Sci., 61, 29-34 (2012)
[Non-Patent Literature 2] Makoto Uyama et al., J. Oleo Sci., 62, 9-16 (2013)
[Non-Patent Literature 3] Yoshikazu Konno, Journal of Japan Cosmetic Engineers, 45, 83-91 (2011)

SUMMARY OF THE INVENTION

Problem to be Solved by the Invention

The present invention has been made in view of the prior art, and an object to be solved thereby is to provide an α-gel forming composition that has a high-stability without causing color development and crystal deposition over time and an α-gel composition using the same.

Means to Solve the Problem

The present inventors conducted extensive studies to solve the above objects and found that a novel α-gel composition is formed when a higher aliphatic alcohol and/or a higher fatty acid, polyoxyethylene sterol ether, and polyoxyethylene dialkyl ester and/or ether having two hydrophobic groups and having 16 or more carbon atoms are contained in a specific ratio, whereby the present invention was accomplished.

More specifically, the composition for forming α-gel according to the present invention, comprises:
(A) 25 to 50% by mass of 1 or more higher aliphatic alcohols having 16 or more carbon atoms and/or higher fatty acids,
(B) 40 to 70% by mass of polyoxyethylene sterol ether represented by the following formula (I):

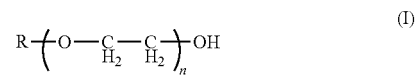

wherein in the formula I, R represents a cholesterol and/or a phytosterol residue, and n represents an integer of 5 to 20,
(C) 5 to 20% by mass of polyoxyethylene dialkyl ester and/or ether represented by the following formula (II):

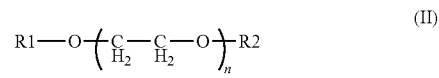

wherein in the formula II, R1 and R2 are a straight-chain aliphatic acid residue or a straight-chain aliphatic alcohol residue having 16 to 24 carbon atoms, and n is an integer of 4 to 15, and forms α-gel when added to an aqueous phase.

Further, the α-gel composition of the present invention is formed by the (A) to (C) in an aqueous phase.

Further, the α-gel composition preferably contains 0.1 to 10% by mass of a double-chain amphiphile having a nitrogen atom based on the active components in the α-gel composition.

Furthermore, the α-gel composition has the double-chain amphiphile having a nitrogen atom preferably consisting of 1 or more selected from phospholipid, lecithin, lysolecithin, ceramide, and a dialkyl quaternary ammonium salt.

The content of a higher aliphatic alcohol having 16 or more carbon atoms and/or a higher fatty acid in the composition for forming α-gel is preferably 25 to 50% by mass in all active components. Examples of the higher aliphatic alcohol having 16 or more carbon atoms include cetyl alcohol, cetostearyl alcohol, stearyl alcohol, behenyl alcohol, and batyl alcohol. Examples of the higher fatty acid include palmitic acid, stearic acid, and behenic acid.

Further, the polyoxyethylene sterol ether of (I) in the composition for forming α-gel preferably has, as the hydrophobic group, phytosterol, cholesterol, and ergosterol, and a polyoxyethylene chain is preferably 5 to 30 mol. Examples include polyoxyethylene (5 mol) phytosterol (e.g., manufactured by Nikko Chemicals, Co., Ltd, Nikkol BPS-5), polyoxyethylene (10 mol) phytosterol (e.g., manufactured by Nikko Chemicals, Co., Ltd., Nikkol BPS-10), polyoxyethylene (20 mol) phytosterol (e.g., manufactured by Nikko Chemicals, Co., Ltd., Nikkol BPS-20), polyoxyethylene (30 mol) phytosterol (e.g., manufactured by Nikko Chemicals, Co., Ltd., Nikkol BPS-30), polyoxyethylene (10 mol) cholesterol (e.g., manufactured by Nihon Emulsion Co., Ltd., Emalex CS-10). The content in all active components is preferably 40 to 70% by mass.

The polyoxyethylene dialkyl ester and/or ether of (II) in the composition for forming α-gel preferably has a straight-chain aliphatic acid residue or a straight-chain aliphatic alcohol residue having 16 to 24 carbon atoms, and a polyoxyethylene chain is preferably 4 to 15 mol. Examples include polyoxyethylene (4 mol) distearate (e.g., manufactured by Nihon Emulsion Co., Ltd., Emalex 200DIS), polyoxyethylene (6 mol) distearate (e.g., manufactured by Nihon Emulsion Co., Ltd., Emalex 300DIS), polyoxyethylene (8 mol) distearate (e.g., manufactured by Nihon Emulsion Co., Ltd., Emalex 400DIS), polyoxyethylene (12 mol) distearate (e.g., manufactured by Nihon Emulsion Co., Ltd., Emalex 600DIS), steareth-4 stearate (e.g., manufactured by Nihon Emulsion Co., Ltd., Emalex SWS-4), steareth-6 stearate (e.g., manufactured by Nihon Emulsion Co., Ltd., Emalex SWS-6), steareth-9 stearate (e.g., manufactured by Nihon Emulsion Co., Ltd., Emalex SWS-9), and polyoxyethylene (8 mol) dibehenyl ether. The binding form of the polyoxyethylene chain and the alkyl group may contain ester, ether, or both of them. The content is preferably 5 to 20% by mass in all active components.

The content of the double-chain amphiphile having a nitrogen atom such as phospholipid, lecithin, lysolecithin, ceramide, or a dialkyl quaternary ammonium salt based on the active components in the α-gel composition is preferably 0.1 to 10% by mass. A content of 0.1% by mass or less results in a poor effect, whereas a content of 10% by mass or more is likely to cause stability problems such as color development and crystal deposition.

Additionally, any amount of the α-gel composition may be blended into the external skin care preparation composition, and generally is preferably 0.1 to 20% by mass as an active component in the α-gel composition in the external skin care preparation.

Effect of the Invention

The α-gel composition and the external skin care preparation composition comprising the same according to the present invention provides refreshing during application, have a high effect on preventing water loss from the internal skin after application (occlusion), and do not raise stability problems such as color development or crystal deposition over time even when blended along with the double-chain amphiphile having a nitrogen atom such as phospholipid, lecithin, lysolecithin, ceramide, or a dialkyl quaternary ammonium salt.

BEST MODE FOR CARRYING OUT THE INVENTION

Hereinafter, the constitution of the present invention is described in detail.

The α-gel composition of the present invention is obtained by melting 25 to 50% by mass of 1 or more higher aliphatic alcohols having 16 or more carbon atoms and/or higher fatty acids, 40 to 70% by mass of polyoxyethylene sterol ether, and 5 to 20% by mass of polyoxyethylene dialkyl ester and/or ether at 70 to 80° C., adding a proportion of 40 to 90% by mass of ion exchange water at 70 to 80° C., stirring and subsequently cooling. Alternatively, the α-gel composition is obtained by, after melting 25 to 50% by mass of 1 or more higher aliphatic alcohols having 16 or more carbon atoms and/or higher fatty acids, 40 to 70% by mass of polyoxyethylene sterol ether, and 5 to 20% by mass of polyoxyethylene dialkyl ester and/or ether at 70 to 80° C., adding and melting the double-chain amphiphile having a nitrogen atom such as phospholipid, lecithin, lysolecithin, ceramide, or a dialkyl quaternary ammonium salt, adding a proportion of 40 to 90% by mass of ion exchange water at 70 to 80° C., stirring and subsequently cooling. The α-gel is generally an aggregate formed by a higher aliphatic alcohol and a hydrophilic surfactant in water, and means α-gel taking the α-structure (by Shoji Fukushima, "sechiru arukoru no butsuri kagaku" ("physical chemistry of cetyl alcohol" in English"), published by Fragrance Journal).

Figure 1:
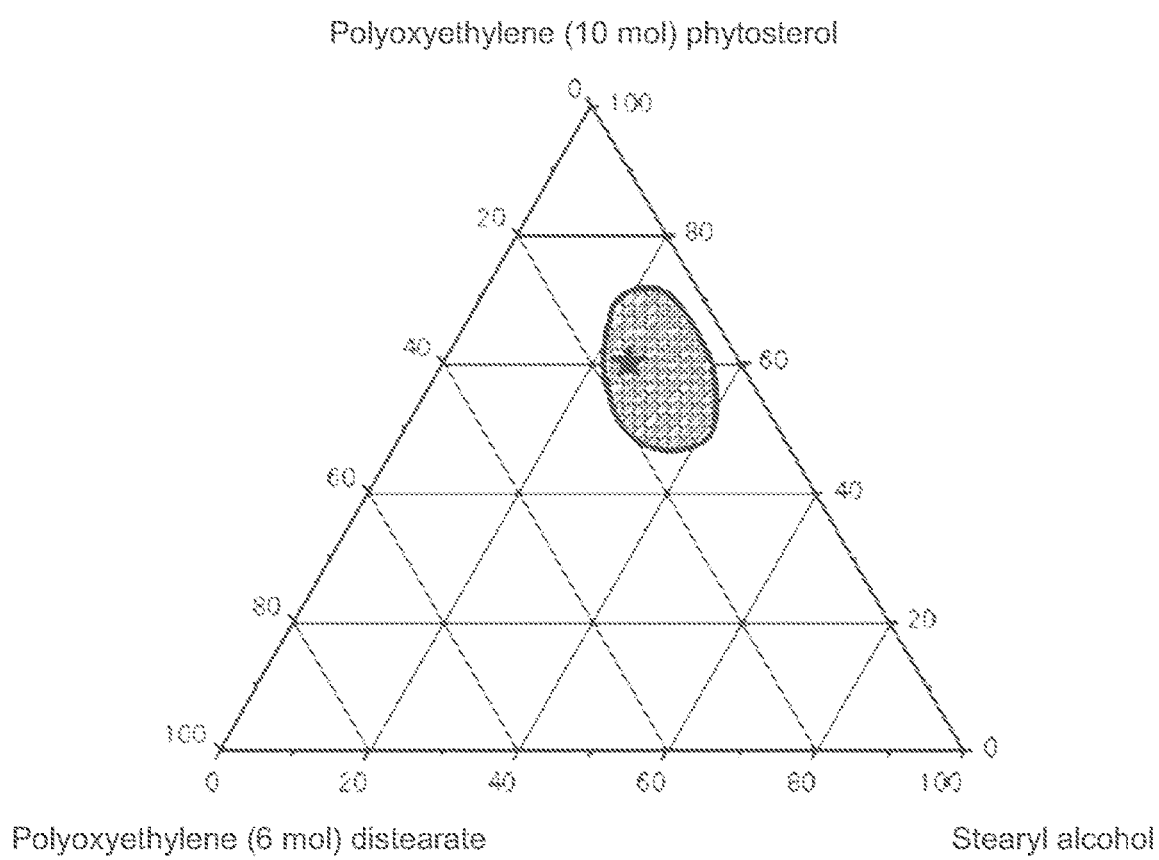
FIG. 1 is a three-component system phase equilibrium diagram of an active component 50% by mass solvent water of polyoxyethylene (6 mol) distearate-stearyl alcohol-polyoxyethylene (10 mol) phytosterol prepared at 25° C. according to the present invention.
Figure 2:
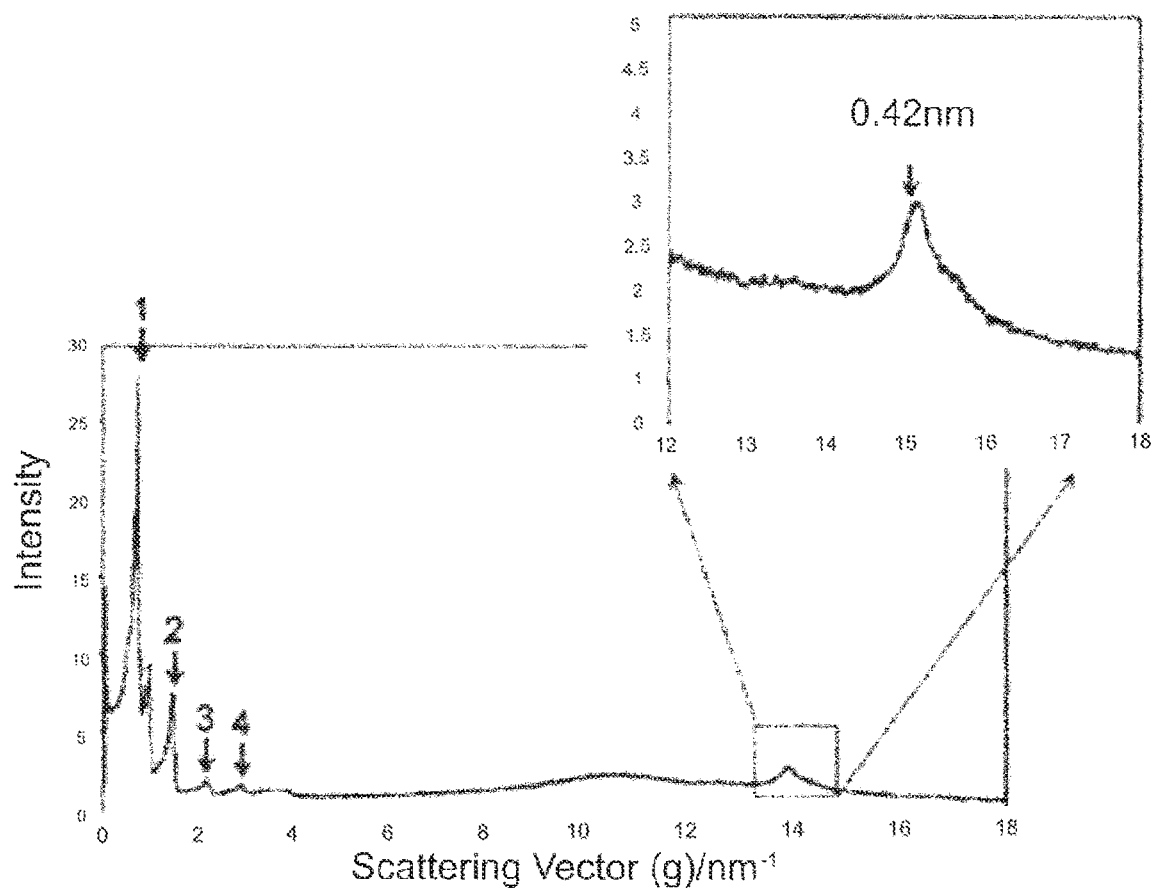
FIG. 2 is an X-ray scattering spectrum at the ★ mark in FIG. 1 according to the present invention.

As a specific example of the α-gel composition, FIG. 1 shows a phase equilibrium diagram of three-component system, which is obtained by respectively selecting 1 or more higher aliphatic alcohols having 16 or more carbon atoms and/or higher fatty acids stearyl alcohol as the polyoxyethylene sterol ether, polyoxyethylene (10 mol) phytosterol (e.g., manufactured by Nikko Chemicals, Co., Ltd, Nikkol BPS-10) as the polyoxyethylene dialkyl esters and/or ether, and polyoxyethylene (6 mol) distearate (e.g., manufactured by Nihon Emulsion Co., Ltd., Emalex 300DIS), making these mixtures a single phase at 70 to 80° C., subsequently adding ion exchange water heated to the same temperature in such a way that the amount of all active components is a proportion of 60% by mass based on the whole amount, and cooling to room temperature. The shaded area in FIG. 1 is a region which has a single melting point peak when measured using a differential calorimeter and obtained scattering peaks (FIG. 2) suggesting the α-gel as a result of X-ray analysis. FIG. 2 is an X-ray scattering spectrum of the composition shown with the ★ mark in FIG. 1.

Figure 3:
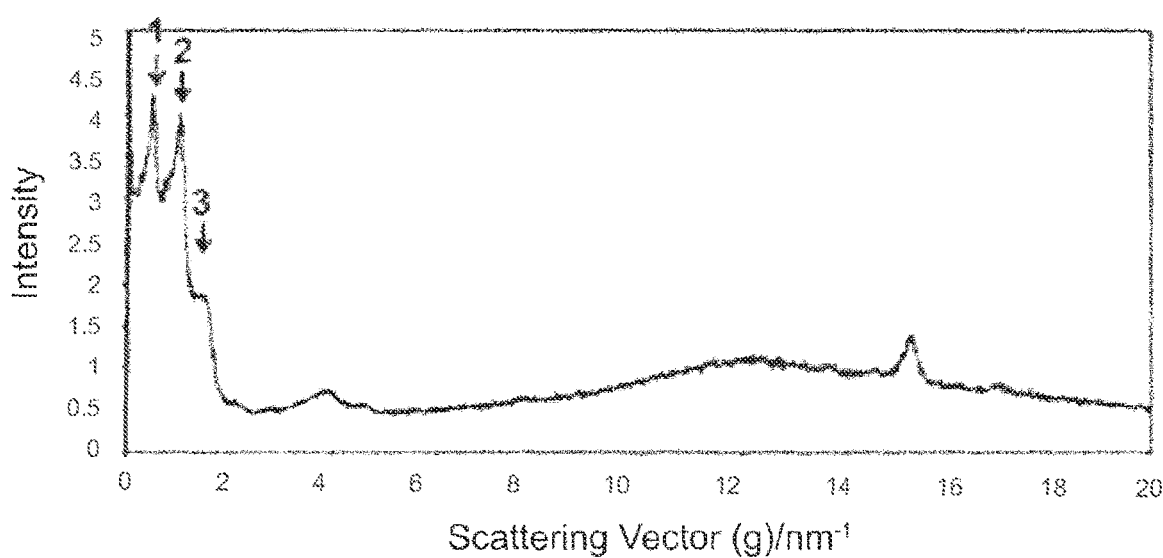
FIG. 3 is an X-ray scattering spectrum of a 50% by mass solvent water of polyoxyethylene (6 mol) distearate/stearate/polyoxyethylene (10 mol) phytosterol=2/2/6 according to the present invention.

Even when stearyl alcohol is replaced with stearic acid, a similar X-ray scattering spectrum suggesting the α-gel was obtained (FIG. 3). As is evident in FIG. 1, the α-gel is confirmed to have been formed in the region of 25 to 50% by mass of stearyl alcohol, 40 to 70% by mass of polyoxyethylene (10 mol) phytosterol, and 5 to 20% by mass of polyoxyethylene (6 mol) distearate.

In the present invention, the above 3 components alone can construct the α-gel, but the double-chain amphiphile, having a nitrogen atom, such as phospholipid, lecithin, lysolecithin, ceramide, or a dialkyl quaternary ammonium salt can also be blended together as needed for the purpose of improving rough skin or the like.

The oil component used in the external skin care preparation of the present invention is not particularly limited, and, for example, a liquid oil and fat, a solid oil and fat, a wax, a hydrocarbon oil, a higher fatty acid, a synthetic ester oil, or a silicone oil can be suitably blended, and further some higher alcohols can also be dissolved in these oils and emulsified. The content in the α-gel-containing external skin care preparation of interest is not particularly limited, and 0.05 to 50% by mass is preferable. A content of 0.05% by mass or less results in a poor effect as the external skin care preparation, whereas a content exceeding 50% by mass causes an undesirable feel when used.

Examples of liquid fats include avocado oil, camellia oil, turtle oil, macadamia nut oil, corn oil, mink oil, olive oil, rapeseed oil, egg yolk oil, sesame oil, par chic oil, wheat germ oil, sasanqua oil, castor oil, linseed oil, safflower oil, cotton seed oil, perilla oil, soybean oil, groundnut oil, brown real oil, torreya oil, rice bran oil, chinese wood oil, jojoba oil, germ oil, and triglycerol.

Examples of solid fats include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, hoof oil, Japan wax, and hydrogenated castor oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether and cetyl palmitate.

Examples of hydrocarbon oils include liquid paraffin, ozocerite, squalene, pristane, paraffin, ceresin, squalane, vaseline, and microcrystalline wax.

Examples of the higher fatty acid include lauric acid, myristic acid, palmitic acid, stearic acid, behenic acid, oleic acid, undecylenic acid, tall acid, isostearic acid, linoleic acid, linolenic acid, eicosapentaenoic acid (EPA), docosahexaenoic acid (DHA).

Examples of the synthetic ester oil include cetyl octanoate, myristyl myristate, glyceryl tri2-ethylhexanoate, pentaerythritol tetra2-ethylhexanoate, dioctyl succinate, and tripropylene glycol dineopentanoate.

Examples of the silicone oil include chain polysiloxanes (e.g., dimethyl polysiloxane, methylphenyl polysiloxane, and diphenyl polysiloxane); cyclic polysiloxanes (e.g., octamethylcyclotetrasiloxane, decamethylcyclopentasiloxane, and dodecamethylcyclohexasiloxane), silicone resins having a three-dimensional network, silicone rubbers, various modified polysiloxanes (amino-modified polysiloxane, polyether-modified polysiloxane, alkyl-modified polysiloxane, and fluorine-modified polysiloxane), and acrylic silicones.

The α-gel-containing external skin care preparation of the present invention can be used, for example, in skin cosmetics, hair cleansers, skin cleansers, and hair styling products applicable to the body such as skins and hair.

The α-gel-containing external skin care preparation of the present invention can further contain, in addition to the essential components described above, components typically used in cosmetics and pharmaceutical products at a content in a range which does not affect the stability. Examples of such a component include powder components, amphoteric surfactants, ionic surfactants, nonionic surfactants, moisturizers, thickeners, coating agent, UV absorbers, sequestering agents, pH adjusters, skin nutrients, vitamins, antioxidants, antioxidant aids, and fragrances.

Examples of powder components include inorganic powder (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate, calcium phosphate, fluorine apatite, hydroxyapatite, ceramic powder, metallic soap (for example, zinc myristate, calcium palimitate, and aluminum stearate), and boron nitride); organic powder (for example, polyamide resin powder (nylon powder), polyethylene powder, polymethylmethacrylate powder, polystyrene powder, styrene-acrylic acid copolymer resin powder, benzoguanamine resin powder, poly(tetrafluroethylene) powder, and cellulose powder); inorganic white family pigment (for example, zinc oxide); inorganic red family pigment (for example, iron titanate); inorganic purple family pigment (for example, mango violet, cobalt violet); inorganic green family pigment (for example, chrome oxide, chrome hydroxide, cobalt titanate); inorganic blue family pigment (for example, ultramarine, iron blue); pearl pigment (for example, titanium oxide coated mica, titanium oxide coated bismuth oxychloride, titanium oxide coated talc, colored titanium oxide coated mica, bismuth oxychloride, argentine); metal powder pigment (for example, aluminum powder, and copper powder); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); natural pigment (for example, chlorophyll, and 6-carotene).

Examples of ampholytic surfactants include imidazoline base ampholytic surfactant (for example, sodium 2-undecyl-N,N,N-(hydroxyethylcarboxymethyl)-2-imidazoline, 2-cocoyl-2-imidazolinium hydroxide-1-carboxyethyloxy)-2-sodium salt; and betaine base surfactant (for example, 2-heptadecyl-N-carboxymethyl-N-hydroxyethylimidazolinium betaine, lauryldimethyl aminoacetate betaine, alkyl betaine, amidobetaine, and sulfobetaine).

Example of ionic surfactants include N-acyl methyl sodium, N-acyl glutamic acid salt, alkyl sulfate, polyoxyethylene alkyl sulfate, fatty acid soap and alkyl quaternary ammonium salt.

Examples of lipophilic nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, and diglycerol sorbitan tetra-2 ethylhexylate); glyceryl polyglyceryl fatty acids (for example, glyceryl monocotton oil fatty acid, glyceryl monoerucate, glyceryl sesquioleate, glyceryl monostearate, glyceryl α,α'-oleate pyroglutamate, and glyceryl monostearate malate); propylene glycol fatty acid esters (for example, propylene glycol monostearate); hydrogenated castor oil derivative; and glyceryl alkyl ether.

Examples of hydrophilic nonionic surfactants include POE-sorbitan fatty acid esters (for example, POE-sorbitan monooleate, POE-sorbitan monostearate, and POE-sorbitan tetraoleate); POE-sorbit fatty acid esters (for example, POE-sorbit monolaurate, POE-sorbit monooleate, POE-sorbit pentaoleate, and POE-sorbit monostearate), POE-glyceryl fatty acid esters (for example, POE-glyceryl monostearate; POE-glyceryl monoisostearate, and POE-glyceryl triisostearate); POE-fatty acid esters (for example, POE-distearate, POE-monodioleate, and ethyleneglycol distearate); POE-alkyl ethers (for example, POE-lauryl ether, POE-oleyl ether, POE-stearyl ether, POE-behenyl ether, POE-2-octyldodecyl ether, and POE-cholestanol ether); pluronic types (for example, Pluronic), POE/POP-alkyl ethers (for example, POE/POP-cetyl ether, POE/POP-2-decyltetradecyl ether, POE/POP-monobutyl ether, POE/POP-hydrogenated lanoline, and POE/POP glycerin ether); tetra POE/tetra POP-ethylenediamine condensation products (for example, Tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, and POE-hydrogenated oil maleate); POE-beeswax/lanoline derivatives (for example, POE-sorbitol beeswax); alkanolamides (for example, coconut oil fatty acid diethanolamide, lauric acid monoethanolamide, and fatty acid isopropanolamide); POE-propyleneglycol fatty acid esters; POE-alkyl amines; POE-fatty acid amides; sucrose fatty acid esters; alkylethoxydimethylamine oxide; and trioleyl phosphoric acid.

Examples of natural water-soluble polymers include plant-based polymer (for example, gum Arabic, gum tragacanth, galactan, guar gum, locust bean gum, gum karaya, carrageenan, pectine, agar, quince seed (cydonia oblonga), algae colloid (brown algae extract), starch (rice, corn, potato, and wheat), and glicyrrhizic acid), microorganisms based polymer (for example, xanthan gum, dextran, succinoglycan, and pullulan), animal-based polymer (for example, collagen, casein, and albumin, gelatine).

Examples of semisynthetic water-soluble polymers include starch-based polymer (for example, carboxymethyl starch, and methylhydroxypropyl starch), cellulosic polymer (methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, micrclrystalline cellulose, and cellulose powder), alginic acid base polymer (for example, sodium alginate, and propylene glycol ester alginate) and sodium pectate.

Examples of synthetic water-soluble polymers include vinyl base polymer (for example, polyvinyl alcohol, polyvinyl methyl ether, polyvinylpyrrolidone, and carboxyvinylpolymer); polyoxyethylene base polymer (for example, polyethylene glycol 20,000, 40,000, and 60,000); Poly (dimethyldiallylammonium halide) type cationic polymer (for example, Merquat100 Merck U.S.A Co. ltd); Copolymerizable type cationic polymers of dimethyldiallylammonium halide and acrylamide (for example Merquat550 Merck U.S.A Co. ltd,); acrylic polymer (for example, sodium polyacrylate, polyethylacrylate, and polyacrylamide); polyethyleneimine; cationpolymer and magnesium aluminum silicate.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid family ultraviolet light absorbers (for example, homomenthyl N-acetylanthranilate); salicylic acid family ultraviolet light absorbers (for example, amyl salicylate, menthyl salicylate, homomenthyl salicylate, octyl salicylate, phenyl salicylate, benzyl salicylate, and p-isopropanolphenyl salicylate); cinnamic acid family ultraviolet light absorbers (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-ß-phenylcinnamate, 2-ethylhexyl α-cyano-ß-phenylcinnamate, and glyceryl mono-2-ethylhexanoyl-diparamethoxy cinnamate); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one.

Example of sequestering agent include 1-hydroxyethane-1,1-diphosphonic acid, 1-hydroxyethane-1,1-diphosphonic acid tetrasodium salt, edetate disodium, edetate trisodium, edetate tetrasodium, sodium citrate, sodium polyphosphate, sodium metaphosphate, gluconic acid, phosphoric acid, citric acid, ascorbic acid, succinic acid, edetic acid and Ethylenediamine hydroxyethyl triacetate trisodium.

Examples of the pH adjuster include buffers such as lactic acid-sodium lactate, citric acid-sodium citrate, and succinic acid-sodium succinate.

Examples of the vitamin include vitamins A, B1, B2, B6, C, E, and derivatives thereof, pantothenic acid and derivatives thereof, and biotin.

Examples of the antioxidant include tocopherols, dibutylhydroxytoluene, butylhydroxyanisol, and gallic acid esters.

Examples of anti-oxidant aids include phosphoric acid, citric acid, ascorbic acid, maleic acid, malonic acid, succinic acid, fumaric acid, cephalin, hexamethaphosphate, phytic acid, and ethylene diamine tetra-acetic acid.

Examples of other blendable components include antiseptic agent (ethylparaben, butylparaben, etc); lightening agent (for example, placental extract, saxifrage extract, and arbutin); blood circulation promotion agent (for example, nicotine acid, nicotine acid benzyl, tocopherol nicotinate, nicotine acid β-butoxy ester, minoxidil, or their analogs, vitamine E type, γ-oryzanol, alkoxycarbonylpyridine N-oxide, capronium chloride, acetylcholine and their derivatives); various extract (for example, ginger, oat, Japanese coptis, lithospermum, birch, loquat, carrot, aloe, mallow, iris, grape, sponge gourd, lily, saffron, cnidium rhizome, ginger, hypericum, restharrow, garlic, red pepper, citrus unshiu, Japanese angelica, Japanese tree peoney, and seaweed); activator agent (for example, pantothenyl ethyl ether, nicotinamide, biotin, pantothenic acid, royal jelly, and cholesterol derivative); and antiseborrheric agent (for example, pyridoxine, and thianthl).

Further, fragrances, scrubbing agents, and the like can suitably be blended in a range which does not affect the stability.

EXAMPLES

Hereinafter, the present invention will be described in further detail in reference with Examples but is not limited thereto. The content is always expressed in % by mass, unless specifically stated otherwise.

[Comparison of Occlusion Effect of the α-Gel]

The compositions of the following Examples and Comparative Examples were prepared at 70° C. using an ultrasonic homogenizer, cooled, subsequently applied homogeneously to paper at a rate of 5 mg/cm2 respectively, and allowed to stand for 1 day. In a thermo-hygrostat (23° C., relative humidity=45%), 5 mL of water was placed in a 25 mL vial, immediately the filter paper was inserted and fixed with the cap of the vial, and an amount of water lost was measured successively. The amount of water evaporated per hour (attenuation % by mass) was defined as water evaporation rate constant (%/hour). Thus, the smaller a water evaporation rate constant (%/hour) is, the higher the ability to retain water is.

Example 1

|  | Content |
| --- | --- |
| (1) Stearyl alcohol | 12.5% |
| (2) Polyoxyethylene (10 mol) phytosterol | 30.0% |
| (3) Polyoxyethylene (6 mol) distearate | 7.5% |
| (4) Ion exchange water | 50.0% |

Example 2

|  | Content |
| --- | --- |
| (1) Stearic acid | 12.5% |
| (2) Polyoxyethylene (10 mol) phytosterol | 30.0% |
| (3) Polyoxyethylene (6 mol) distearate | 7.5% |
| (4) Ion exchange water | 50.0% |

Example 3

|  | Content |
| --- | --- |
| (1) Behenyl alcohol | 15.0% |
| (2) Polyoxyethylene (20 mol) phytosterol | 30.0% |
| (3) Polyoxyethylene (4 mol) distearate | 5.0% |
| (4) Ion exchange water | 50.0% |

Comparative Example 1

|  | Content |
| --- | --- |
| (1) Behenyl alcohol | 34.1% |
| (2) Sodium N-stearoyl methyltaurate | 15.9% |
| (3) Ion exchange water | 50.0% |

Comparative Example 2

|  | Content |
| --- | --- |
| (1) Behenyl alcohol | 30.0% |
| (2) Polyoxyethylene (20 mol) behenyl ether | 20.0% |
| (3) Ion exchange water | 50.0% |

Comparative Example 3

|  | Content |
| --- | --- |
| (1) Stearyl alcohol | 12.5% |
| (2) Polyoxyethylene (10 mol) phytosterol | 30.0% |
| (3) Soybean hydrogenated retinol | 7.5% |
| (4) Ion exchange water | 50.0% |

Results

Results are shown in Table 1. As is evident in Table 1, the α-gel s of the present invention (Examples 1 to 3) were revealed to have higher occlusion effects than the α-gel bases of Comparative Examples 1 to 3, in which behenyl alcohol and sodium N-stearoyl methyltaurate, behenyl alcohol and polyoxyethylene (20 mol) behenyl ether, stearyl alcohol, polyoxyethylene (10 mol) phytosterol, and soybean hydrogenated retinol, were used.

TABLE 1

| Occlusion effect of each α-gel base | |
| --- | --- |
| Test base | Water loss rate constant (%/hour) |
| Ion-exchange water (Reference) | 0.143 |
| Example1 | 0.032 |
| Example2 | 0.041 |
| Example3 | 0.040 |
| Comparative Example1 | 0.075 |
| Comparative Example2 | 0.086 |
| Comparative Example3 | 0.055 |

[Viscosity Stability Test]

Further, the bases of Examples 1 to 3 and Comparative Examples 1 to 3 were respectively diluted 10-fold with ion exchange water at 75° C., stored each at 0 to 50° C., the viscosity over time was retained at 30° C. for 30 minutes or longer, and subsequently measured using a B type viscometer (mPa·s).

Results

Results are shown in Table 2. As is evident in Table 2, the viscosities were stable in Examples 1 to 3 and Comparative Example 3, but the viscosities were found to have increased over time in Comparative Examples 1 and 2. Comparative Example 3, of which the viscosity was stable, was found to have a changed smell.

TABLE 2

Viscosity changes over time of Examples 1 to 3 and Comparative Examples 1 to 3

| Time elapsed, Temperature conditions | Example 1 | Example 2 | Example 3 | Comparative Example 1 | Comparative Example 2 | Comparative Example 3 |
|---|---|---|---|---|---|---|
| Day1 | 2260 | 2530 | 2760 | 7450 | 5630 | 2600 |
| 1 Month 0° C. | 2450 | 2710 | 2830 | 17600 | 9600 | 2730 |
| 1 Month 25° C. | 2550 | 2680 | 2740 | 20000 | 10100 | 2800 |
| 1 Month 37° C. | 2460 | 2650 | 2690 | 14200 | 18700 | 2750 |
| 1 Month 50° C. | 2400 | 2480 | 2670 | 14000 | 15700 | 2580 |

Results

[Smell Stability]

The bases of Examples 4 to 6 and Comparative Examples 4 to 6 were respectively diluted 10-fold with ion exchange water at 75° C., stored each at 50° C., and the smell after 1 month had passed was determined on the following criteria by trained panelists.

Criteria

A: No problem, B: smell slightly changed, C: smell changed

Example 4

| | Content |
|---|---|
| (1) Stearyl alcohol | 12.5% |
| (2) Polyoxyethylene (10 mol) phytosterol | 30.0% |
| (3) Polyoxyethylene (6 mol) distearate | 6.0% |
| (4) Soybean hydrogenated retinol | 1.5% |
| (5) Ion exchange water | 50.0% |

Example 5

| | Content |
|---|---|
| (1) Stearic acid | 12.5% |
| (2) Polyoxyethylene (10 mol) phytosterol | 30.0% |
| (3) Polyoxyethylene (6 mol) distearate | 7.0% |
| (4) Ceramide III | 0.5% |
| (5) Ion exchange water | 50.0% |

Example 6

| | Content |
|---|---|
| (1) Behenyl alcohol | 15.0% |
| (2) Polyoxyethylene (20 mol) phytosterol | 30.0% |
| (3) Polyoxyethylene (4 mol) distearate | 4.8% |
| (4) Distearyl quaternary ammonium chloride | 0.2% |
| (5) Ion exchange water | 50.0% |

Comparative Example 4

| | Content |
|---|---|
| (1) Behenyl alcohol | 34.1% |
| (2) Sodium N-stearoyl methyltaurate | 14.4% |
| (3) Soybean hydrogenated retinol | 1.5% |
| (4) Ion exchange water | 50.0% |

Comparative Example 5

| | Content |
|---|---|
| (1) Behenyl alcohol | 30.0% |
| (2) Polyoxyethylene (20 mol) behenyl ether | 19.5% |
| (3) Ceramide III | 0.5% |
| (4) Ion exchange water | 50.0% |

Comparative Example 6

| | Content |
|---|---|
| (1) Stearyl alcohol | 12.5% |
| (2) Polyoxyethylene (10 mol) phytosterol | 30.0% |
| (3) Distearyl quaternary ammonium chloride | 7.5% |
| (4) Ion exchange water | 50.0% |

Results

Results are shown in Table 3. As is evident in Table 3, it was revealed that the use of the α-gel compositions of the present invention inhibits the change in smell of the double-chain amphiphile having a nitrogen atom such as phospholipid, lecithin, lysolecithin, ceramide, or a dialkyl quaternary ammonium salt.

TABLE 3

Smell determination results of each α-gel base

| Test Base | Smell determination |
|---|---|
| Example4 | A |
| Example5 | A |
| Example6 | A |
| Comparative Example 4 | C |
| Comparative Example 5 | B |
| Comparative Example 6 | C |

Hereinafter, the present invention is further described in reference with more specific Examples, but is not limited thereto.

Example 7

| Emulsion | Content (% by mass) |
| --- | --- |
| (1) Stearyl alcohol | 1.3 |
| (2) Polyoxyethylene (10 mol) phytosterol | 3.0 |
| (3) Polyoxyethylene (6 mol) distearate | 0.6 |
| (4) Dipropylene glycol | 5.0 |
| (5) Fragrance | 0.1 |
| (6) Pentaerythritol tetra2-ethylhexanoate | 2.0 |
| (7) α Olefin oligomer | 3.0 |
| (8) Dimethylpolysiloxane (manufactured by Shin-Etsu Chemical Co., Ltd., Silicone KF96-A6T) | 2.0 |
| (9) Purified vaseline | 1.0 |
| (10) 1,3-Butylene glycol | 2.0 |
| (11) Phenoxyethanol | 0.5 |
| (12) Glycerin | 4.0 |
| (13) Carboxy vinyl polymer | 0.03 |
| (14) Potassium hydroxide | 0.01 |
| (15) Tranexamic acid | 0.1 |
| (16) Citric acid | 0.02 |
| (17) Sodium citrate | 0.08 |
| (18) Ion exchange water | Balance |

(Production Method)

The emulsification was carried out by a routine method to obtain the above emulsion. The obtained emulsion had a high occlusion effect, was refreshing, and had good viscosity stability and smell stability.

Example 8

| Essence | Content (% by mass) |
| --- | --- |
| (1) Sodium N-stearoyl methyltaurate | 0.01 |
| (2) Stearyl alcohol | 0.13 |
| (3) Polyoxyethylene (10 mol) phytosterol | 0.3 |
| (4) Polyoxyethylene (6 mol) distearate | 0.06 |
| (5) Liquid paraffin | 0.78 |
| (6) Methylphenylpolysiloxane (manufactured by Shin-Etsu Chemical Co., Ltd., Silicone KF56) | 0.2 |
| (7) Fragrance | 0.02 |
| (8) Polyoxyethylene (14 mol) polyoxypropylene (7 mol) dimethyl ether | 0.5 |
| (9) Glycerin | 3.0 |
| (10) Dipropylene glycol | 5.0 |
| (11) 1,3-Butylene glycol | 3.0 |
| (12) Citric acid | 0.02 |
| (13) Sodium citrate | 0.08 |
| (14) EDTA2Na•2H2O | 0.01 |
| (15) General alcohol 95% | 5.0 |
| (16) Phenoxyethanol | 0.5 |
| (17) Ion exchange water | Balance |

(Production Method)

The emulsification was carried out by a routine method to obtain the above essence. The obtained essence had a high occlusion effect, was refreshing, and had good viscosity stability and smell stability.

Example 9

| Emulsion | Content (% by mass) |
| --- | --- |
| (1) Stearyl alcohol | 1.3 |
| (2) Polyoxyethylene (10 mol) phytosterol | 3.0 |
| (3) Polyoxyethylene (6 mol) distearate | 0.6 |
| (4) Soybean hydrogenated retinol | 0.2 |
| (5) Isoprene glycol | 4.5 |
| (6) 1,4-Butanediol | 1.5 |
| (7) Fragrance | 0.09 |
| (8) Glyceryl tristearate | 2.5 |
| (9) Squalane | 4.5 |
| (10) Dimethylpolysiloxane (manufactured by Shin-Etsu Chemical Co., Ltd., Silicone KF96-A6T) | 1.0 |
| (11) Propylene glycol | 7.0 |
| (12) Erythritol | 1.3 |
| (13) Dynamite glycerin | 6.0 |
| (14) Phenoxyethanol | 0.3 |
| (15) Xanthan gum | 0.5 |
| (16) Sodium hexametaphosphate | 0.03 |
| (17) Ion exchange water | Balance |

(Production Method)

The emulsification was carried out by a routine method to obtain the above emulsion. The obtained emulsion had a high occlusion effect, was refreshing, and had good viscosity stability and smell stability.

Example 10

| Sun block cream | Content (% by mass) |
| --- | --- |
| (1) Behenyl alcohol | 1.5 |
| (2) Polyoxyethylene (20 mol) phytosterol | 3.0 |
| (3) Polyoxyethylene (4 mol) distearate | 0.5 |
| (4) Ceramide II | 0.2 |
| (5) Dipropylene glycol | 6.0 |
| (6) Fragrance | 0.08 |
| (7) Glyceryl tri2-ethylhexanoate | 2.0 |
| (8) Di-2-ethylhexyl succinate | 3.0 |
| (9) 2-Ethylhexyl p-methoxycinnamate | 5.0 |
| (10) Avobenzone | 3.0 |
| (11) Bis-ethylhexyloxyphenol methoxyphenyl triazine | 1.0 |
| (12) 1,3-Butylene glycol | 5.0 |
| (13) Phenoxyethanol | 0.5 |
| (14) Glycerin | 9.0 |
| (15) EDTA-trisodium salt | 0.1 |
| (16) Erythritol | 0.1 |
| (17) Citric acid | 0.02 |
| (18) Sodium citrate | 0.08 |
| (19) Ion exchange water | Balance |

(Production Method)

The emulsification was carried out by a routine method to obtain the above sun block cream. The obtained sun block cream had a high occlusion effect, was refreshing, and had good viscosity stability and smell stability.

Example 11

| Cream | Content (% by mass) |
| --- | --- |
| (1) Stearyl alcohol | 2.5 |
| (2) Polyoxyethylene (10 mol) phytosterol | 6.0 |
| (3) Polyoxyethylene (6 mol) distearate | 1.2 |
| (4) 1,3-Butylene glycol | 6.5 |
| (5) Fragrance | 0.05 |
| (6) Dimethylpolysiloxane (manufactured by Shin-Etsu Chemical Co., Ltd., Silicone KF96-A6T) | 7.4 |
| (7) Squalane | 4.0 |

-continued

| Cream | Content (% by mass) |
|---|---|
| (8) Purified vaseline | 1.0 |
| (9) Dipropylene glycol | 5.0 |
| (10) Phenoxyethanol | 0.5 |
| (11) Glycerin | 7.0 |
| (12) EDTA-trisodium salt | 0.1 |
| (13) Camomile extract | 0.1 |
| (14) Citric acid | 0.02 |
| (15) Sodium citrate | 0.08 |

(Production Method)

The emulsification was carried out by a routine method to obtain the cream. The obtained cream had a high occlusion effect, was refreshing, and had good viscosity stability and smell stability.

What is claimed is:

1. An α-gel forming composition, comprising
    (A) 25 to 50% by mass of at least one component selected from the group consisting of higher aliphatic alcohols having at least 16 carbon atoms and higher fatty acids;
    (B) 40 to 70% by mass of a polyoxyethylene sterol ether of formula (I), $$R-(OCH_2CH_2)_n-OH \quad (I)$$

wherein R is a cholesterol residue or a phytosterol residue, and n is an integer from 5 to 20;
    (C) 5 to 20% by mass of at least one component selected from the group consisting of polyoxyethylene dialkyl esters and ethers of formula (II):

$$R1O-(CH_2CH_2O)_n-R2 \quad (II)$$

wherein R1 and R2 are independently residue selected from the group consisting of straight-chain aliphatic acid residues having 16 to 24 carbon atoms and straight-chain aliphatic alcohol residues having 16 to 24 carbon atoms, and n is an integer from 4 to 15; and
    wherein said α-gel forming composition forms an α-gel with water.

2. An α-gel composition formed by adding water to the α-gel forming composition according to claim 1.

3. The α-gel composition, according to claim 2, further comprising 0.1 to 10% by mass of a double-chain amphiphile based on the total amount of (A) to (C);
    wherein said amphiphile has at least one nitrogen atom.

4. The α-gel composition, according to claim 3, wherein:
    said amphiphile is at least one molecule selected from the group consisting of phospholipid, lecithin, lysolecithin, ceramide, and a dialkyl quaternary ammonium salt.

5. An external skin care preparation for skin, comprising said α-gel composition according to claim 2.

* * * * *